US00PP29618P3

(12) United States Plant Patent
Timbery

(10) Patent No.: US PP29,618 P3
(45) Date of Patent: Aug. 21, 2018

(54) ***LOMANDRA* PLANT NAMED 'MURU'**

(50) Latin Name: *Lomandra longifolia*
Varietal Denomination: Muru

(71) Applicant: Muru Mittigar, Penrith South (AU)

(72) Inventor: Deborah Timbery, Penrith South (AU)

( * ) Notice: Subject to any disclaimer, the term of this patent is extended or adjusted under 35 U.S.C. 154(b) by 0 days.

(21) Appl. No.: 15/530,256

(22) Filed: Dec. 15, 2016

(65) Prior Publication Data

US 2017/0181353 P1 Jun. 22, 2017

(30) Foreign Application Priority Data

Dec. 16, 2015 (AU) ..... PBR 2015/347

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Samuel R. McCoy, Jr.

(57) ABSTRACT

'Muru' is a distinctive cultivar of *Lomandra longifolia* which is characterized by variegated foliage comprised of green striations, white striations and broad white margins. The new variety propagates successfully by division and tissue culture and has shown to be uniform and stable in the resulting generations from asexual propagation.

1 Drawing Sheet

Latin name of the genus and species: The Latin name of the genus and species of the novel variety disclosed herein is *Lomandra longifolia.*

Variety denomination: The inventive variety of *Lomandra longifolia* disclosed herein has been given the variety denomination 'Muru'.

CROSS REFERENCE TO RELATED APPLICATIONS

This application claims priority to the Australian Plant Breeders Rights application number 2015/347, filed on Dec. 16, 2015, which is herein incorporated by reference.

BACKGROUND OF THE INVENTION

The present invention relates to a new and distinct perennial variety of *Lomandra longifolia*, which has been given the variety denomination of 'Muru'. Its market class is PLT/373. 'Muru' is intended for use in landscaping and as a decorative plant.

Parentage: 'Muru' is a seedling selection resulting from an open-pollination of an unnamed *Lomandra longifolia* plant. In February of 2010, the inventor discovered a variegated seedling of *Lomandra longifolia* in a crop of seedlings being produced for nursery stock at a wholesale plant nursery in Penrith South, NSW, Australia. This seedling was isolated and grown to a mature size to assess the stability of the variegation and overall plant vigor. In April of 2011, the plant was divided to increase numbers and test its hardiness and stability. It has proven a strong growing variegated form of the species with no off types observed. This new and distinctive cultivar was given the name 'Muru'.

Asexual Reproduction: 'Muru' was first asexually propagated in April of 2011 by division of the plant's crown in Penrith South, NSW, Australia and has since been asexually reproduced by meristematic tissue culture propagation. The distinctive characteristics of the inventive 'Muru' variety have proven to be stable through five generations and clones so produced maintain the distinguishing characteristics of the original plant.

SUMMARY OF THE INVENTION

'Muru' is a distinctive cultivar of *Lomandra longifolia* which is characterized by variegated foliage comprised of green striations, white striations and broad white margins.

BRIEF DESCRIPTION OF THE FIGURES

The FIGURE illustrates, as true as is reasonably possible to obtain in color photographs of this type, an exemplary 'Muru' specimen of approximately 24 months of age in a 250 mm nursery pot, grown at a commercial plant breeding facility in Clarendon, NSW, Australia.

BOTANICAL DESCRIPTION OF THE PLANT

The following is a detailed botanical description of a new and distinct variety of a *Lomandra* ornamental plant known as 'Muru'. Plant observations were made on plants grown in Bellingen, NSW, Australia. Unless indicated otherwise, the descriptions disclosed herein are based upon observations made in early December 2016 of 24 month old 'Muru' plants grown outdoors, under 30 percent shade, from rooted cuttings in 250 mm nursery pots filled with soilless potting media, maintained with granular slow release fertilizer and regularly watered with overhead irrigation. No pest and disease measures were taken.

Those skilled in the art will appreciate that certain characteristics will vary with older or, conversely, younger plants. 'Muru' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 2001 edition.

A botanical description of 'Muru' and comparisons with the seed parent and several similar varieties of common knowledge are provided below.

General plant description:

*Plant habit.*—Grass-like perennial with arched to weeping foliage; rhizomatous plant forming a dense tussock.

*Reproduction.*—Dioecious; male of the species.

*Height.*—25 cm as measured.

*Width.*—50 cm as measured.

*Bloom period.*—Spring.

*Propagation.*—Propagation is accomplished by dividing the crown of the plant and also by way of meristematic tissue culture propagation.

*Crop time.*—Time to initiate rooting is approximately 4 weeks; time to develop a rooted cutting is approximately 8 to 10 weeks. An average crop time is approximately 6 to 9 months to produce a mature and marketable 1-gallon nursery container, beginning with a rooted cutting.

*Environmental tolerances.*—Evergreen in USDA Hardiness Zones 8 through 11 and potentially root hardy in USDA Zone 7; adapt to temperatures ranging from approximately 23 degrees Fahrenheit to 113 degrees Fahrenheit. Shade and drought tolerant once established.

*Pest and disease susceptibility or resistance.*—Neither resistance nor tolerance to pests and diseases known to effect *Lomandra longifolia* have been observed.

Roots: Densely rooting; roots are fibrous and distributed evenly throughout the soil profile, from shallow to deep.

Rhizomes: Short, 3 to 4 cm; rhizome color with the leaf sheath removed is white, nearest to RHS 155D; surface texture of the rhizome is smooth.

Foliage:

*Type.*—Evergreen.

*Shape.*—Linear; grass-like.

*Division.*—Simple.

*Arrangement.*—Whorled around an indistinguishable culm.

*Aspect.*—Arched to weeping.

*Apex.*—Tridentate. The leaf apex may become locally necrotic in response to moisture stress.

*Base.*—Sheathed attachment to the culm.

*Margins.*—Entire.

*Texture, adaxial surface.*—Glabrous; smooth.

*Texture, abaxial surface.*—Glabrous; smooth; glaucous.

*Mature leaf dimensions.*—7.5 mm wide and 350 mm long, on average. The leaf is generally a uniform width, narrowing only slightly from base to apex.

*Juvenile foliage color, adaxial surface.*—Parallel variegation; the majority of the leaf surface is yellow-green, RHS 144A, with fine pale yellow-white striations, nearest to RHS 153C; broadly margined pale yellow-white, nearest to RHS 153C.

*Juvenile foliage color, abaxial surface.*—Parallel variegation; with glaucosity removed, the majority of the leaf surface is yellow-green, RHS 144A, with fine pale yellow-white striations, nearest to RHS 153C; broadly margined pale yellow-white, nearest to RHS 153C.

*Mature foliage color, adaxial surface.*—Parallel variegation; comprised of green striations (RHS 137A), creamy white striations (nearest to RHS 150D) and broad creamy white margins (nearest to RHS 150D).

*Mature foliage color, abaxial surface.*—Parallel variegation; comprised of green striations (RHS 137A), creamy white striations (nearest to RHS 150D) and broad creamy white margins (nearest to RHS 150D).

*Venation.*—Parallel.

*Vein color, adaxial surfaces.*—Indistinguishable from surrounding foliage.

*Vein color, abaxial surfaces.*—Indistinguishable from surrounding foliage.

Inflorescence:

*Type.*—Racemes containing small clusters of male flowers; some flowers are sessile to the rachis while others are borne on pedicels of varying length.

*Dimensions.*—90 mm long and 20 mm long.

*Natural flowering season.*—Spring.

*Overall dimensions.*—Up to 90 mm long, including the peduncle and rachis.

*Quantity.*—Very floriferous; inflorescences may potentially arise from every shoot.

*Attitude.*—Semi-erect to erect.

*Peduncle.*—Dimensions — Up to 50 mm long and 2 mm in diameter. Attitude — Semi erect. Strength — Strong. Texture — Smooth. Color — 144A.

*Pedicels.*—Dimensions — Up to 12 mm long and 1.25 mm in diameter. Strength — Strong. Texture — Smooth. Color — 145A.

Bud:

*Dimensions.*—Approximately 2 mm long and 2 mm wide.

*Bud shape.*—Rounded.

*Bud color.*—Dull yellow, nearest to RHS 10B.

*Rate of bud opening.*—Slow.

Flower:

*Shape.*—Cupuliform; cup-shaped.

*Lastingness of flowers.*—Approximately 10 days.

*Persistence.*—Non-persistent.

*Aspect.*—Erect.

*Fragrance.*—Moderately fragrant; sweet and honey-like.

*Perianth.*—Calyx — Shape — Ovate. Dimensions — Approximately 1 mm. Color — Dull yellow, nearest to RHS 10B. Texture — Smooth. Sepals — Arrangement — Rotate. Quantity — Three. Margin — Entire. Apex — Aristate. Base — Obtuse. Texture — Smooth. Sepal color, mature, upper surface — 165C. Sepal color, mature, under surface — 165C. Corolla — Arrangement — Rotate; petals unfused. Dimensions — Approximately 2 mm in diameter and 4 mm deep. Petals — Quantity — Three. Arrangement — Rotate. Dimensions — Approximately 1.5 mm long and 1.0 mm wide. Shape — Ovate. Margin — Entire. Apex — Acute. Base — Obtuse. Texture — Smooth. Color when opening, upper side — Nearest to 150C. Color when opening, under side — Nearest to 150C. Color when fully opened, upper side — 10B. Color when fully opened, under side — 10B. Bracts — Shape — Needle-shaped.

Length — range in length from 6 to 9 mm. Apex — Acute. Margin — Entire. Color — 160D.

Reproduction organs: Not observed.

Seed: Flower are male; seed is not produced.

Comparisons with the parent plant: Plants of the new cultivar 'Muru' exhibit green and white variegated foliage, whereas the seed parent, a female *Lomandra longifolia* plant, does not exhibit foliage variegation.

Comparisons with the most similar variety of common knowledge: Plants of the new cultivar 'Muru' exhibit green and white variegated foliage, whereas the commercial variety, *Lomandra* sp. 'LMV100' (U.S. application Ser. No. 11/810,224, now abandoned), exhibits green and yellow variegation.

That which is claimed is:

1. A new and distinct variety of *Lomandra longifolia* named 'Muru', substantially as described and illustrated herein.

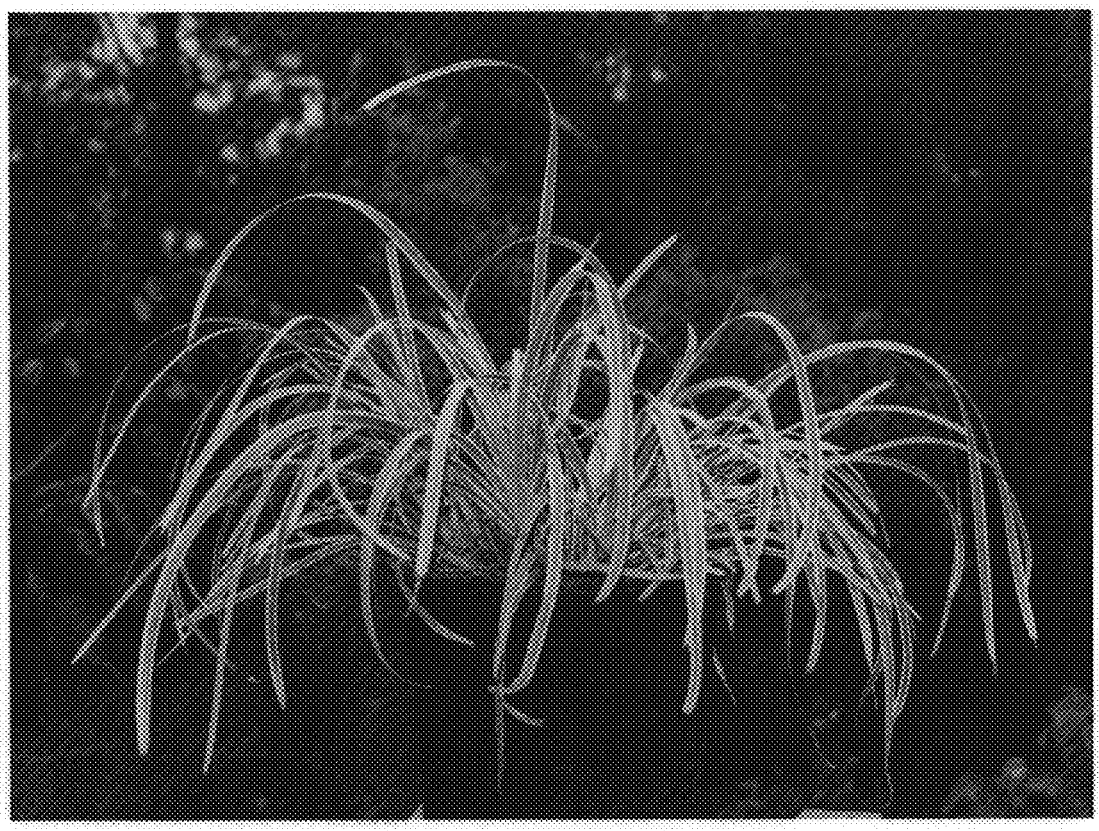

* * * * *